(12) United States Patent
Cervera Sabater et al.

(10) Patent No.: US 7,927,097 B2
(45) Date of Patent: Apr. 19, 2011

(54) PLASTIC BRACKET WITH MECHANICAL RETENTION AND PRODUCTION METHOD THEREOF

(75) Inventors: Alberto Cervera Sabater, Alcorcón (ES); Julio Bravo De Pedro, Alcorcón (ES); Sabino Azcárate Leturia, Alcorcón (ES); Luis Gerardo Uriarte Ibarrola, Alcorcón (ES)

(73) Assignee: Euroortodoncia, S.L., Madrid (ES)

( * ) Notice: Subject to any disclaimer, the term of this patent is extended or adjusted under 35 U.S.C. 154(b) by 535 days.

(21) Appl. No.: 11/922,224

(22) PCT Filed: Jun. 17, 2005

(86) PCT No.: PCT/ES2005/000346
§ 371 (c)(1),
(2), (4) Date: Dec. 14, 2007

(87) PCT Pub. No.: WO2006/136618
PCT Pub. Date: Dec. 28, 2006

(65) Prior Publication Data
US 2009/0325117 A1 Dec. 31, 2009

(51) Int. Cl.
*A61C 7/00* (2006.01)
(52) U.S. Cl. .......................................... 433/9

(58) Field of Classification Search .................. 433/8, 9, 433/10; 264/16
See application file for complete search history.

(56) References Cited

U.S. PATENT DOCUMENTS

| | | | | |
|---|---|---|---|---|
| 4,219,617 | A * | 8/1980 | Wallshein | 433/8 |
| 4,604,057 | A * | 8/1986 | Viglietti | 433/9 |
| 4,936,773 | A * | 6/1990 | Kawaguchi | 433/9 |
| 5,267,854 | A * | 12/1993 | Schmitt | 433/8 |
| 5,622,494 | A * | 4/1997 | Andreiko et al. | 433/9 |
| 5,653,588 | A * | 8/1997 | Moschik | 433/8 |
| 5,820,371 | A * | 10/1998 | Forster | 433/9 |
| 6,071,117 | A * | 6/2000 | Andreiko et al. | 433/9 |
| 6,190,165 | B1 * | 2/2001 | Andreiko et al. | 433/9 |

* cited by examiner

*Primary Examiner* — Ralph A Lewis
(74) *Attorney, Agent, or Firm* — Defillo & Associates, Inc; Evelyn A. Defillo

(57) ABSTRACT

The invention relates to a bracket which is intended for use in orthodontics and which is made entirely from plastic using an injection molding process. The inventive bracket comprises the basic elements of any bracket, such as the base which is fixed or cemented to the tooth, the arch groove in the mesial-distal direction and flanges for standard wire ligatures or elastomers. The invention is essentially characterised in that, as with metal brackets, the fixing base provides mechanical retention and, as such, does not have to be coated with any type of chemical additive during the cementing procedure.

4 Claims, 6 Drawing Sheets

PLASTIC BRACKET WITH MECHANICAL RETENTION AND PRODUCTION METHOD THEREOF

The present invention is related to a bracket of use in orthodontics and its process of manufacturing, which, although being exclusively made of plastics by injection moulding, has properties that are comparable to the metallic ones as far as hardness, finishing and mechanical safetying is concerned.

BACKGROUND OF THE INVENTION

It is known that in the orthodontic treatments, such pieces like brackets, buccal tubes or apparatuses of this type must be adhered to the teeth by cementing. The specific parts to be joined are in the anterior or posterior surface of the tooth and one surface of the bracket which is known as the dental surface of the base. The base is intimately joined to the so called bracket body wherein the retention groove of the orthodontic arc is generally to be found.

Taking into consideration the manufacturing materials, the brackets can be metallic, ceramic or plastic, but due to economic and aesthetic reasons the trend is more and more to produce them with plastics since the material is cheaper than metal or ceramics and also can achieve colours similar to the one of the teeth or yet better make them transparent, which gives them an added aesthetic value. A technological challenge of the producers of orthodontic devices is therefore to achieve a plastic bracket that provides for characteristics similar to the metallic ones with respect to deformation resistance and/or breaking strength and retention properties, but moreover being more aesthetic and showing less manufacturing cost. It is also important to take into consideration the manufacturing procedure, which can be by means of mechanising or injection moulding, the latter being less expensive.

The queries to be considered when it comes to achieve a plastic bracket with the aforementioned properties are fundamentally: the shape of the base, the shape of the bracket body, the type of plastic in the moulding process for its manufacturing.

It is a primary object of the present invention to achieve that the bracket has a base of mechanical retention. If one analyzes the base, a first important aspect to consider is the adherence power thereof with the tooth, said base having to support forces within the range of 50-100 newtons. This is not easy to achieve, taking into consideration the material and the small size of the piece. Because of that the form of the base and particularly that of the dental surface have been the object of several patents, since the retention strength as well as the easiness of implantation depend on said form. The retention may be chemical or mechanical and is a factor that the professional takes into consideration when he chooses a determined type of bracket; since the chemical retention comprises the additional step of applying a liquid to the base for the joining of the base with the cementing material can be produced.

The body of the bracket has generally some retention wings and a groove for the arc that conform to a characteristic geometric figure in which the zones with a greater deformation or breaking probability are delimited when the bracket is subjected to the tensions of the arch that is introduced into the groove and to the chewing. It is known that the plastic is easier to be deformed and broken than metal or ceramics, but there exists moreover the additional problem that a plastic bracket may suffer a progressive degradation within the time due to hydrolysis, that in the same time causes mechanical defects and a progressive change of the colour of the plastic up to turning opaque. The degradation by hydrolysis is avoided by means of a finishing of the part that is as perfect as possible, and here comes to play a role the material selected as well as the moulding process selected.

It has been said already that the form of the base depends on the union of the bracket with the tooth, and that this form has been the object of different patents. The U.S. Pat. No. 4,544,353 discloses an apparatus that improves the technique of joining by direct contact the teeth with an orthodontic device. The joining technique by direct contact consists in applying the adhesive onto the dental surface of the base; putting the base covered with the adhesive onto the tooth; and cleans the residual adhesive. Due to the form of the base of the orthodontic devices, which were existing up to that moment, this operation became somewhat difficult because of the sliding of the glue and the bracket during the positioning thereof on the tooth's surface, and moreover having to clean the remaining adhesive. In the mentioned patent, this problem is resolved by means of a base, which has a flange with an angle between 90° to 70° which extends along its whole periphery, thereby defining a cavity that receives the adhesive and that in addition to cutting off any exceed of adhesive it impedes its falling during the positioning of the tooth.

The U.S. Pat. No. 5,295,824 discloses a plastic bracket that improves the joining process of a plastic bracket with the teeth, in which the union surface of the tooth is covered with a mixture of acrylic monomers and solvents that attack and dissolve the plastic substrate, thereby being spread within the same. Once the dental surface of the base is covered, the bracket and the mixture are heated in order to volatilize the solvents and monomers of lower molecular weight thereby achieving a layer of acrylic material that is predominantly monomeric. This first layer acts as a first adhesive and improves the joining strength when the same is performed with dental adhesives such as the acrylic ones. The appropriate solvents cited in said patent are benzene, chloroform, acetone, dichloromethane or any other acting as solvent of plastics composing the bracket. The plastic brackets made of polycarbonate are very appropriate for using this method.

An objective being searched for through the years is to achieve plastic brackets whose base has a dental surface sufficiently rough in order to not needing to vulcanize the surface before fixing it to the tooth. The process is tried to be analogous to the one of the metallic brackets which in general have some grooves in the dental surface of the base that are sufficient to obtain a cementing that provides for the adequate retention strength.

The U.S. Pat. No. 6,071,117 proposes a method for manufacturing orthodontic devices made of plastic by means of injection moulding; the surface of the base of the bracket projects itself outwards with such forms like cylinders or rectangular prisms that are easily configurable since they are created in a mould. This form of surface of the base expects the joining surface of the bracket's base with the fixing cement to be the largest possible. A first problem is caused because of the fact that the surfaces of the aforementioned forms cannot be rough since if the mould would be designed in this way, some breakage could be caused while taking the bracket out of the mould. A consequence of this is that the achieved geometry by means of the moulding is not sufficient to obtain the adequate strengths if the retention is mechanical. To resolve this problem, a second step is carried out, which is to deform the geometry of the base in the external part by means of heat or ultrasonic energy and to provide for spaces with the shape of an inverted cone next to the external surface, that facilitate the mechanic retention of the base of the bracket with the surface of the tooth.

Possibly because of problems with a mechanical retention, the U.S. Pat. No. 6,109,165 of the same applicant of the aforementioned patent discloses a similar method with respect to the form of the base and the deformation process, that includes one step more, which is posterior to the foregoing, and consists in bombarding with particles in order to make them crash against the external part of the base's projections.

The method disclosed in said foregoing U.S. Pat. No. 6,071,117 and U.S. Pat. No. 6,190,165 has the problem of to the step of moulding there is the need of causing the deformation, with what, although the deformation is carried out in deformation stations that control the process, the heating element may reach up to 400° F. (204° C.), which might cause deformations in the whole bracket.

A second object of the present invention is to obtain mechanical facilities which are equivalent to those of the metallic bracket. If we consider the problem that is posed by the hardness of the plastic bracket, or what is the same, the ability of resistance to deformations or breakage, this one has been fundamentally treated in two ways. One of them is to look for the appropriate type of plastic and the other one is to introduce into its interior metallic structures that reinforce the points that have to support higher tensions.

When the type of plastic is mentioned, it is not only talked about whether it is from the class of polycarbonates, polysulfones, polyethersulfones or others, but what is meant is that the plastic may or may not be charged with other elements. The charge doesn't involve the mixing with plastic of inorganic materials like the alum or silica, although it may also be charged with organic or metallic materials, always with the purpose of augmenting the resistance of the assembly.

The U.S. Pat. No. 5,254,002 as well as some embodiments of the aforementioned U.S. Pat. No. 6,071,017 and U.S. Pat. No. 6,190,165 disclose a method for reinforcing the plastic in which the plastic is a refilled by dispersing in its interior some inorganic materials such like glass particles. Nevertheless, this method of dispersion of particles inside the plastic be it from glass, alum or metallic ones, has the problem that microbreakages are caused due to the fact that, when being injected, the mixture has a high temperature and as every component has a different coefficient of expansion, some deformations are caused as it cools down. This effect is more intense in the narrower zones of the geometry of the body which on the other hands are those being more likely to break, and in the superficial zones as well, which causes an increment of the non desired effect of hydrolysis.

In order to alleviate the aforementioned effect of microbreakages the U.S. Pat. No. 6,358,043 introduces into the mixture organic materials by mixing polycarbonate as basic element and an elastomer from styrene as a hardening element of a particle size of 0.1 µm to 10 µm. Nevertheless, the hardening does not seem to be sufficient, as it includes a reinforcing metallic sheet which extends inserted between the wings in the direction of the groove. One can list a series of problems of the brackets that have elements embedded with metallic reinforcement when fabricated by means of injection moulding. Among said problems one can list some like deformations in the plastic matrix, chips, movements of said sheet during the manufacturing process which even can cause the movement of said sheet during its use in an orthodontic treatment process, and also the raising of its price.

BASIC DESCRIPTION OF THE INVENTION

The present invention proposes a plastic bracket, which by achieving sufficient resistance for avoiding breakage, a good finishing to palliate the effects of hydrolysis and that the plastic material does not loose its transparency, disposes of mechanical retention for the cemented material and no need for the use of a chemical additive that improves the fastening of the bracket, palliating the problems of the previous technique.

In order to achieve the goal the procedure comprises several steps, which are:

selection of the material, which has to be "uniform"

calculation of the size of the bracket, whereby said size depends on the material with which it is going to be built, and on the resistance to deformation or breakage to be achieved.

performing tests on the form of the base since it has to be taken into consideration that the form of said base must be the adequate one to be fabricated in an injection mould and to be extracted out of said mould without breakages or detachments, and that said force also depends on the size and the material with which it is built;

an appropriate design of the mould for it to have an optimal injection point, and therewith an adequate evacuation of gases thereby avoiding accumulation in the zones that would remain weakened, an orientation of the fibers that provides for more hardness to the assembly and a lesser deformation through contraction.

creation of a roughness of the grooves of the base by means of bombarding with particles, in order to achieve the retention of the cementing product on the tooth.

The selected materials have been polycarbonate, polysulfone, and polyethersulfone, because they behave well against hydrolysis and when the finishing of the part is the adequate one, they keep the transparent colour without tending to turn opaque with the passing of time. They also resist sterilization with autoclave and have been used many times for sanitary products. These materials have been selected without mixtures nor charges of reinforcing materials for the chemical structure of the whole piece be and there are no zones of different hardness due to a bad distribution of the charges, especially in the narrowing surfaces or zones.

Thereby, considering that the selected material is one without charges, and one is sure about that the physical and chemical characteristics of the part to be fabricated are the same in all of the zones, the problem is to achieve that the fabricated piece from this material, of which the form is essentially known in the state of the art has some predetermined characteristics of resistance to deformation and breakage.

This has been achieved by means of studies based on the finite element simulation, such that by knowing which is the material and the characteristics of a resistance to deformation and breakage an optimal form of the geometry of the bracket and the minimal size of thereof is achieved for the initial premises to be accomplished.

Said simulations have been performed by means of an application software of the enterprise Cosmosworks and after numerous trials, it has been come to the conclusion that plastic models can be produced, which even being somewhat larger than the metallic ones fulfill the indicated characteristics, and in addition have a size sufficiently small to be utilized in orthodontic treatments.

Once the size of the bracket is known, the form of the base is analyzed, so that this one has good mechanical characteristics of retention. The retention bases of brackets fabricated by means of moulding have typically some grooves in the mesial-distal direction, which have to be designed so that they let the air go out and thereby permit the total entrance of the cementing material, do not deform themselves with the tensions produced by the chewing and have certain roughness so that they compensate the contractions of the cement as it dries.

Taking into consideration that:

the grooves of the base must have the above mentioned characteristics;

the cementing materials have a contraction that is in the range of between 1.65% up to 4.16%; and size and form of the bracket are known through the calculations performed in the second design step.

different base arrangements have been made with respect to the quantity of grooves, length of the groove, depth of the groove, distance between bracket base grooves and form more or less concave of the bracket base grooves. Through variation of the parameters a great number of possible arrangements have been obtained, all of which have been tested by traction tests with an INSTRON machine in order to determine the optimal configuration with respect to the configuration parameters.

From the aforementioned tests some values of the parameters that configure the form of the base have been obtained, which are comprised between maximal and minimal values, within of which an equal or greater retention force than the predetermined one is achieved.

The moulding process is of great importance, so that the bracket keeps all properties of the materials on which the calculations of the previous steps have been made. The objectives are:

that the piece has an uniform finishing and hydrolysis does not take place or at least that this one is minimum.

That in the injection process tensions caused by a difficult exhaust of the gases do not accumulate, which would cause a non uniform contraction and a final form which is not according to the expected characteristics that have been calculated in previous steps.

By means of a simulation software tests have been performed in order to see which is the optimal injection point, and where the gas exhausting must be located in, so that once taken out of the mould, the piece has the required characteristics of uniformity of material, uniformity of contraction and finishing of surface.

To assure that the retention force does not diminish with the maximal contraction of 4.16% the distance between bracket base grooves is narrowed by means of a sand blasting once the piece is taken out of the mould and cooled.

The results and characteristics related to the five steps of the process in order to achieve the bracket of the present invention, will be seen more in detail in a description of one preferred embodiment of the invention.

BRIEF DESCRIPTION OF THE DRAWINGS

For a better comprehension of the object of the present invention a practical embodiment of the present invention will be described based upon the attached drawings, wherein

FIG. 5 shows how the depth p of the bracket base grooves depends on the angle a.

PREFERRED EMBODIMENT OF THE INVENTION

As previously said, the variables considered for obtaining the bracket of the present invention are: manufacturing material, size of the bracket, form of the base, design of the mould and bombarding with sand blasting of said base.

The selected materials have been polycarbonate, polysulfone and polyethersulfone, because they behave well against the hydrolysis and when the finishing of the piece is the adequate one they keep the transparent colour without tending to turn opaque with the passing of time, resisting moreover to autoclave temperatures. These materials are not charged with any other material because the size of the bracket is about 8 $mm^3$ and nowadays it is not easy to know which are the properties of a composed structure when dealing with such a small element because the measures for hardness are not sufficiently developed and contrasted due to the fact that the measuring markers for said measures neither are contrasted.

Figure 1:
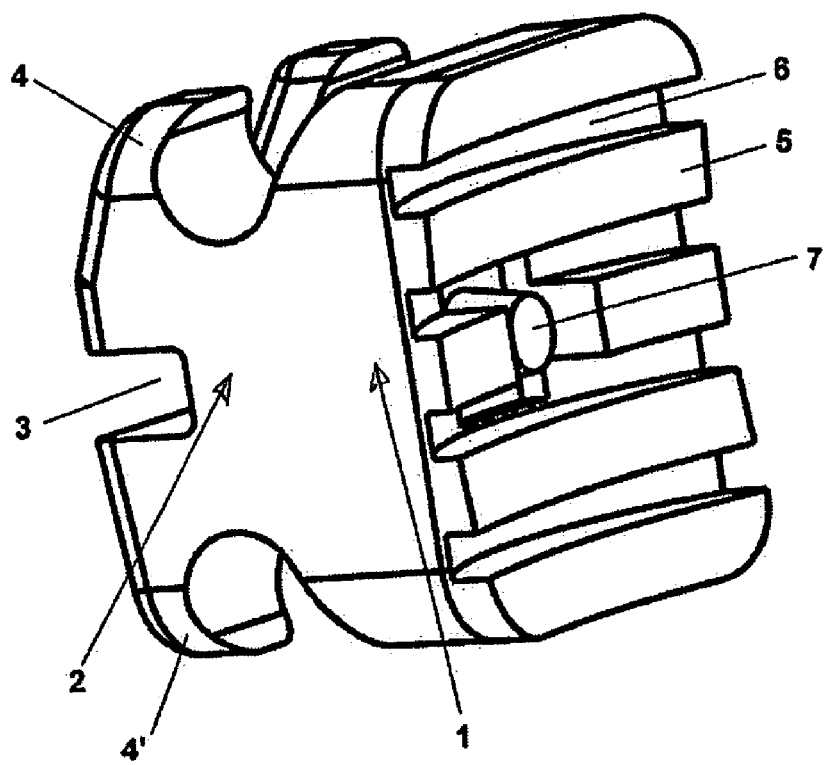
FIG. 1 is a perspective view of the bracket from a lateral posterior point, wherein the form of the base can be seen.

The bracket of the present invention is represented in FIG. 1 and consists of two portions which are a retention base 1 and a bracket body 2, whereby the bracket body 2 has an arch wire slot groove 3 that holds the arch and some wings for upper 4 and lower 4(') ligatures, wherein the retention base has bracket base grooves 6 made in the surface and some supporting strips in the tooth 5, the injection spot 7 being located in the geometric midpoint of the base.

In the preferred embodiment polysulfone has been used, and taking its physical and chemical properties as a starting point the necessary tests have been performed in order to calculate the adequate dimensions of the bracket aiming that said one has an adequate deformation resistance and strength against breakage.

Figure 2:
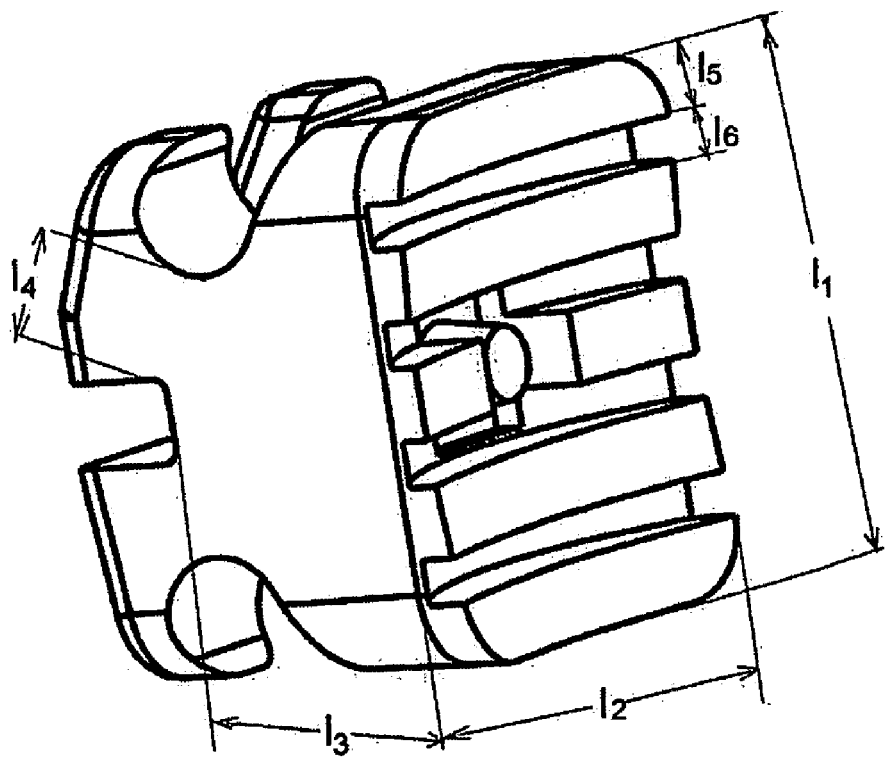
FIG. 2 is the same view (As) than that of the bracket of the FIG. 1 for showing the dimensions of the construction parameters off the bracket.
Figure 3:
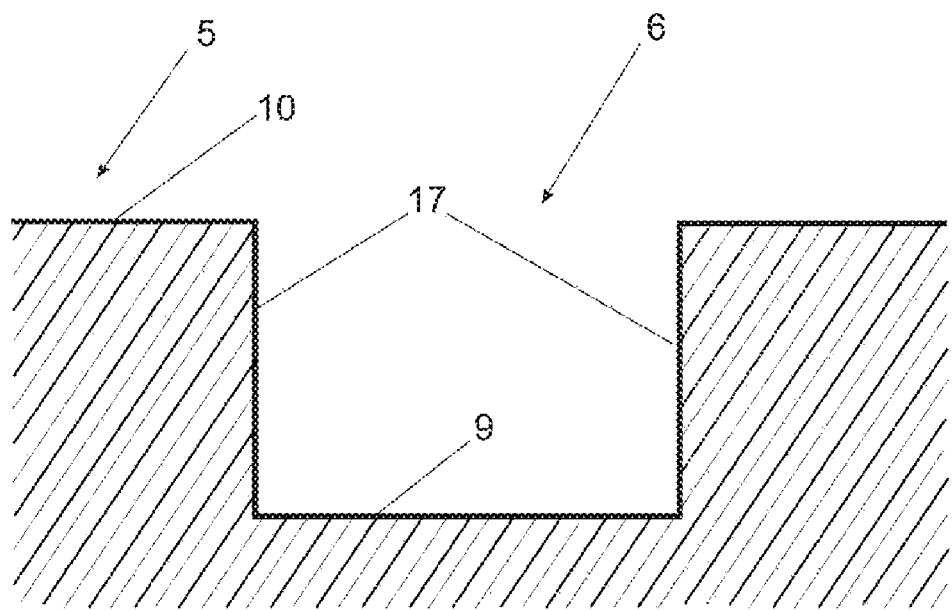
FIG. 3 is a vertical cross-section of one of the grooves of the base of the bracket of FIG. 1.

The dimensions to be taken into consideration (see FIG. 2) in order to obtain a bracket that fulfils the aforementioned object are; the occlusal-gingival length $I_1$, the mesial-distal length $I_2$, the distance $I_3$ from the bottom of the surface of the bracket base groove up to the strip base of the ligature; and the distance $I_4$ from the intersection of lateral and bottom sides up to the surface of the arch wire slot of the ligature.

The results obtained in the performed tests have been the following:

3.3 mm<occlusal-gingival length $I_1$<4.5 mm;

2.8 mm<mesial-distal length $I_2$<3.6 mm;

0.9 mm<distance bottom of the surface of the bracket base groove–strip base of the arch wire slot $I_3$<2.0 mm;

0.7 mm<distance intersection of lateral and bottom sides of the arch wire slot–surface of the ligature $I_4$<2.0 mm;

wherein for the preferred embodiment the values selected have been:

occlusal-gingival length I1=3.5 mm;

mesial-distal length I2=3.1 mm;

distance bottom of the surface of the bracket base groove–strip base of the arch wire slot $I_3$=1.8 mm; and distance intersection of lateral and bottom sides of the arch wire slot–surface of the ligature $I_4$=0.75 mm.

Once the optimal form and size of the bracket is known, the goal is to obtain a base that has a form which is capable of achieving the mechanical retention of the cementing material standing traction forces of at least 50 Newtons. The first conditioning factor of the form of the bracket base grooves 6 of the base is that it can be carried out by injection moulding.

The first conditioning factor assumes that the piece comes out of the mould without causing any deterioration of it, therefore said bracket base grooves 6 not being allowed to have a conical or inverted prismatic form, and thereby the form of the bracket base grooves 6 being limited. The FIG. 1 shows the retention base, which is formed by some supporting strips in the tooth 5 that define the external surface, and some bracket base grooves 6. The form of the bracket base grooves 6 is one of the fundamental points in order to achieve the objective of the present invention, which is, like previously said, to achieve a mechanical retention.

The FIGS. 3-7 show the form of said bracket base grooves 6. As can be seen in the FIG. 3 the bracket base grooves 6 consist of two planar lateral sidewalls 17 and the posterior wall 9 which has a concave form of a circumference arc, while the supporting strips in the tooth 5 are composed of said lateral walls 17 and an anterior wall 10 also with the concave form of a circumference arch. The lateral walls 17 are substantially parallel to allow the way out of the injection mould and the anterior wall has a greater curvature than the posterior wall 9 such that the resin used in the cementing operation with the tooth occupies the largest possible surface and therewith achieves the predetermined adherence value of 50 Newton.

Figure 4:
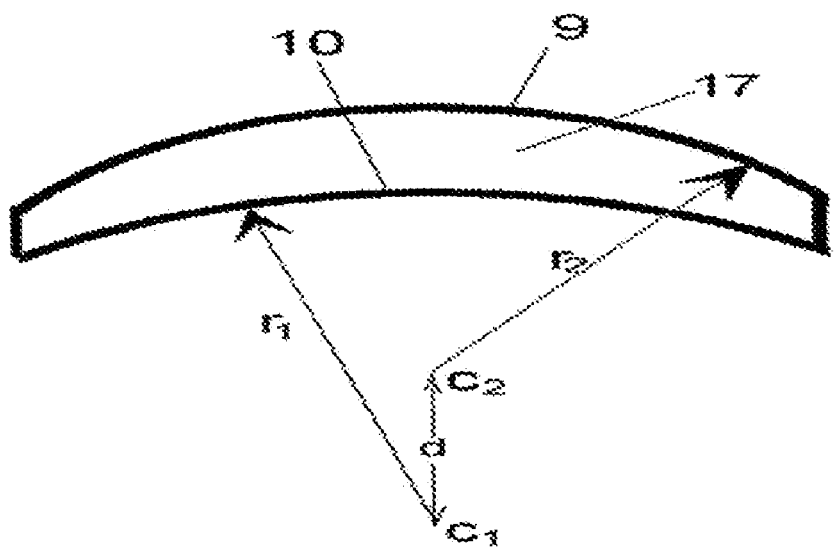
FIG. 4 shows the form of the sides of the bracket base grooves, whereby said form depends on the length of the radiuses r1 r2 and on the distance d between the centers, $C_1$, $C_2$.
Figure 5:
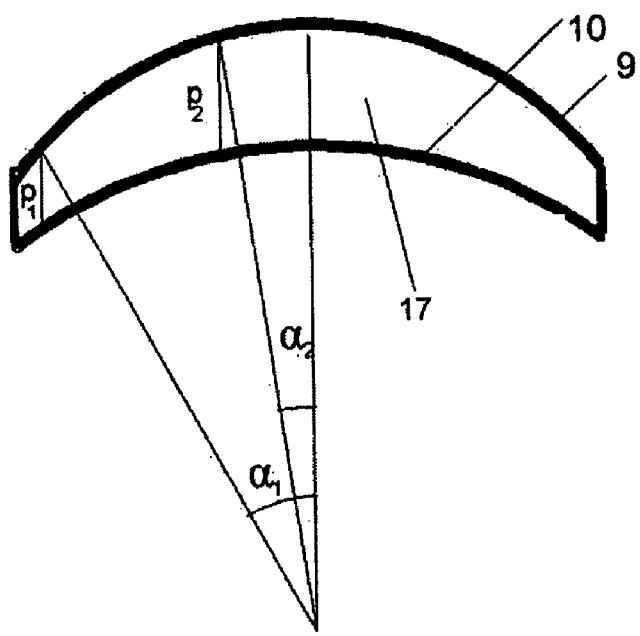
Figure 6:
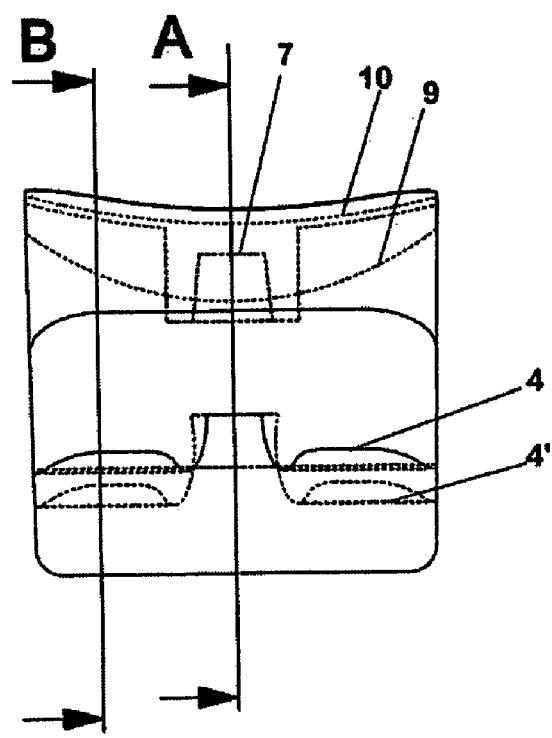
FIG. 6 is a top view of the bracket.
Figure 7:
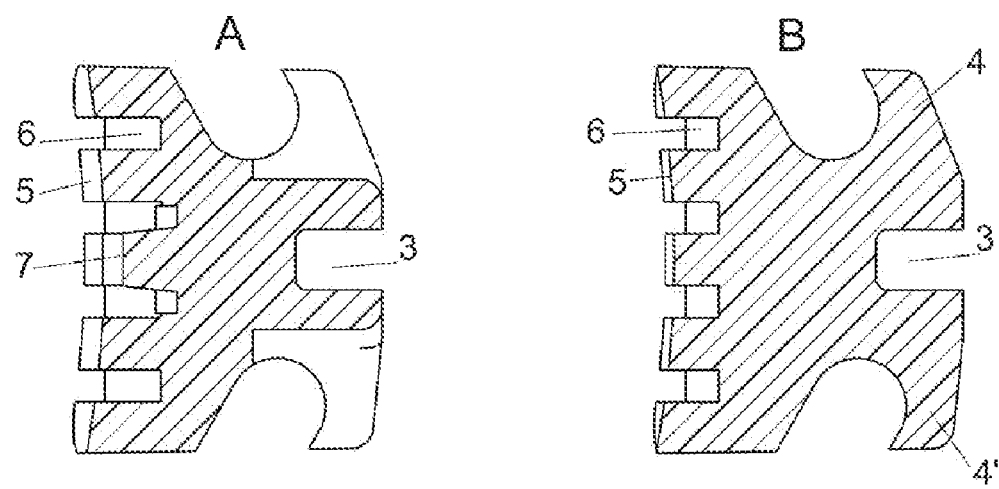
FIG. 7 shows the vertical cross-sections carried out in the plans A and B according to FIG. 5

The FIGS. 4 y 5 show the form of the lateral planar walls 17 which shape the bracket base grooves 6, whereby the grade of concavity of the posterior 9 and anterior 10 walls depends on the centers c, c2 and the (Radii-Check This) radiuses $r_1$, $r_2$, and also of the depth of the bracket base groove 6 depends on the distance between the centers $c_1$ and $c_2$. The depth of the bracket base groove 6 is greater in the symmetric centre (plan A of the FIG. 6) and decreases as it approaches the lateral ends (plan B of the FIG. 6), as can be seen in the FIGS. 5, 7 and 8.

Based on the foregoing, and taking into account the following variables:

number of bracket base grooves 6;
the occlusal-gingival length $I_1$;
the mesial-distal length $I_2$
the width of the supporting strip the in the tooth $I_5$;
the width of the groove $I_6$; and
the width of the bracket base groove 6, which is variable with respect to the angular position and which can be specified by the differences of the values of the curvature radiuses, the aforementioned parameters have been being changed, and a series of different brackets have been produced. The retention strength of each one of them being tested in an INSTRON-machine, coming to the conclusion that for determined measures, predetermined goals are achieved (feasibility of manufacturing by means of injection moulding and mechanical retention)

The values obtained that make the marked target possible, among which is the bracket of the preferred embodiment, can be summarized by means of the following formulas:

3≦number of bracket base grooves≦6;

0.22 mm≦width of the bracket base groove $I_6$≦0.4 mm;

0.45 mm≦width of the supporting strip in the tooth $I_5$ $I_5$≦1 mm; wherein the width of the bracket base groove $I_6$ the width of the supporting strip in the tooth $I_5$;

0.5 mm≦depth in the centre of the bracket 25≦0.7 mm; wherein the depth of the bracket base groove $I_6$ depends on $r_1$ y $r_2$ as well as on the distance between centers wherein 6 mm≦$r_1$≦20 mm, 2 mm≦$r_2$≦5 mm and $r_2$≦($r_1$-2).

Once the total geometry of the bracket is determined, the next step is to achieve a manufacturing method by means of injection moulding, which achieves a piece that does not have weak points, which can be caused by an inadequate orientation of the fibres, accumulation of gases or through contraction deformations in the cooling process.

Figure 8:
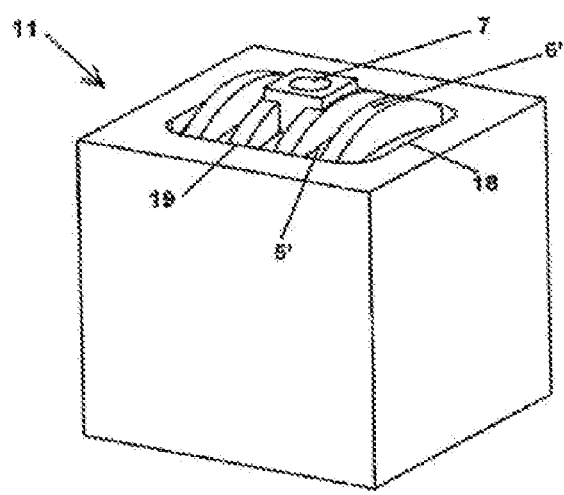
FIG. 8 is a perspective view of the male mould used in the making by injection moulding that gives form to the base of the bracket of FIG. 1.
Figure 9:
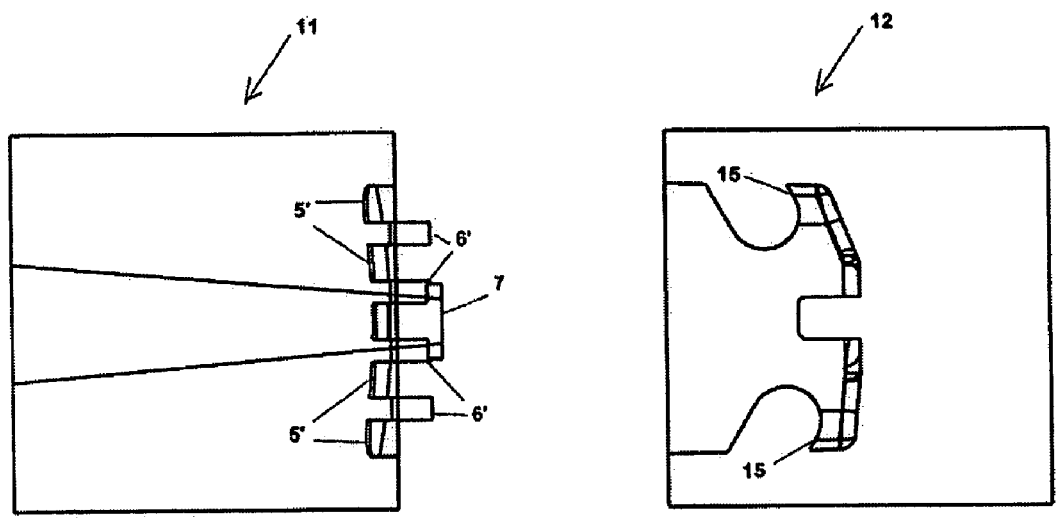
FIG. 9 shows in schematic way the two parts composing the manufacturing mould of the bracket, male for the base and cavity for the body.

The moulding is carried out by means of two die halves which are joined with a slide system in order to be able to eject the piece. Said die halves are:

A male of the base 11 illustrated in the FIGS. 8 and 9, which generates the form of the retention base 1 and in which a protruding part 6' can be seen, which will be the cause of the form of the bracket base groove 6 and some cavities 5' which generate the supporting strips in the tooth 5, wherein the male of the base is limited by an occlusal-gingival edge 19, a mesial-distal edge 18, the injection spot 7; and a cavity in the body 12 illustrated in the FIG. 9, which, as being refilled, generates the parts of the body of the bracket 2, which, as already known, are the retention arch wire slot 3 and the wings 4, 4', wherein the body's cavity is limited by and an occlusal-gingival edge, and a distal mesial edge the coincide with that of the male of the base 11.

In order to reinforce the protruding parts (6') of the male of the base (11) a reinforcing rip(?) (not shown) is provided, which is positioned perpendicularly between the lateral walls (17).

Figure 10:
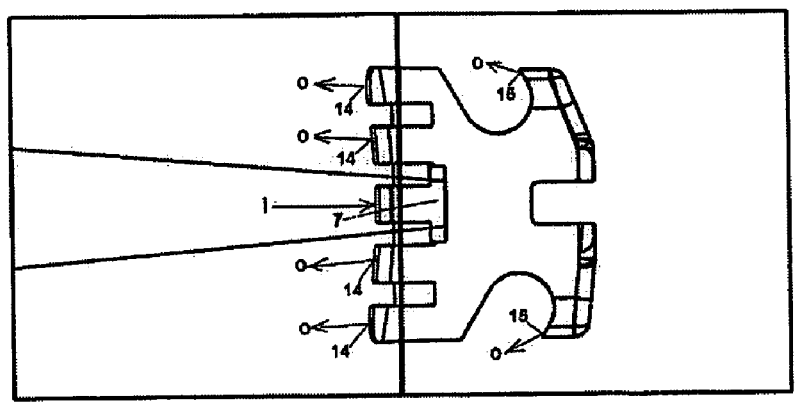
FIG. 10 shows the junction of the mould male with the cavity in an injection moulding process, indicating the injection point by the arrow "i" and the gas exhausting points by arrows "o".

The lengths of the occlusal-gingival edge and of the mesial-distal male of the base 11 and of the cavity of the body are identical and have complementary forms in order to be able to join closely like shown in FIG. 10.

By means of a specific simulation software the injection spots of the plastic and the exhausting spots for the gases, which are generated during the injection, have been searched for, and so to achieve the most appropriated with the goal to achieve that the bracket has an uniform finishing, that no tensions are accumulated in its structure, and then dealing the cooling process no contractions are caused, which deform some parts with more intensity than other of the bracket.

The FIG. 10 illustrates the obtained results:

One sole injection spot located in the place referred by the number 8, with spots for the exhaust of gases in the male of the base referred with the number 14 and exhaust spots in the cavity of the body referred with the number 15.

The last step of the process is carried out in order to compensate the contraction of the cementing resin during its drying. This contraction is approximately of 10%, so that what is intended is to reduce the width of the bracket base grooves 6 in said 10%. This is achieved by means of a corundum blasting with particles of 120-180 microns at 20 psi, 10 cm of distance, during 2 sec, which causes ripplings in the walls, which in addition to cause the effect of reducing the width of the bracket base groove 6, causes a larger retention surface, because it has a corrugated surface, which has a larger extension than when being flat.

Figure 11:
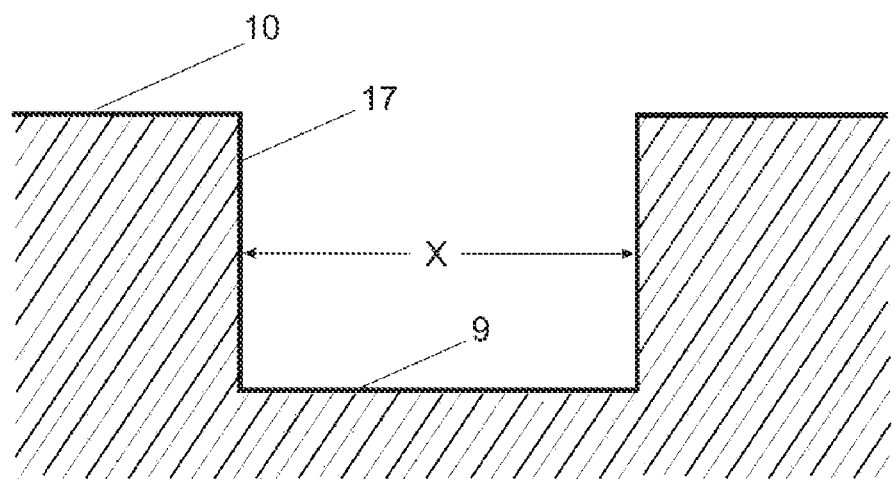
FIG. 11 shows in a schematic way a section of a zone next to a bracket base groove before and after having been subjected to a sand blasting.
Figure 11:
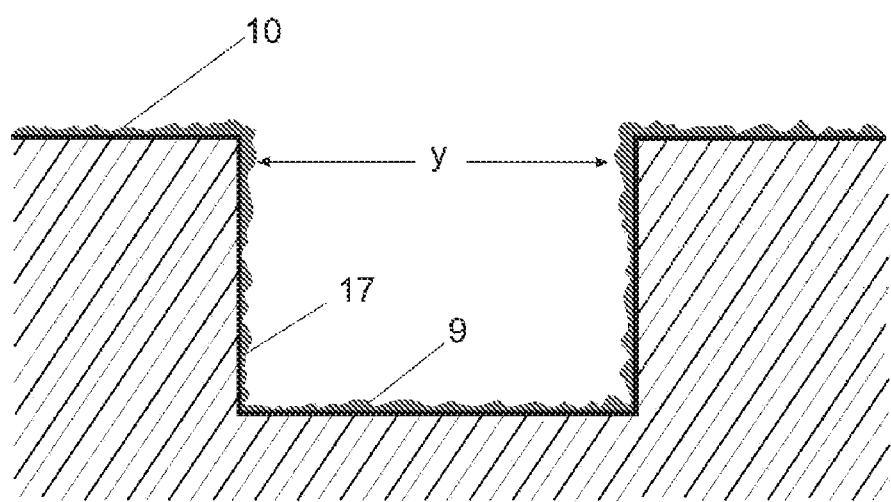

FIG. 11 shows the difference of the surfaces in the zones 9, 10 and 17 of the bracket before being blasted and after being blasted, which evidently is greater due to the rugosities caused, but in addition the blasting has to achieve that y 0.9x, wherein x is the width of the bracket base groove 6 before the sand blasting, and y is the width of said groove 6 after said sand blasting, in order to compensate the contraction of the cementing resin.

Once sufficiently described the nature of the present invention, as well as a preferred embodiment of the same, it is only left to add that both its form as well as the materials and performance of the same are subjected to modifications, as long as they do not affect substantially the characteristics which are claimed in the following CLAIMS.

The invention claimed is:

1. A bracket for its use in orthodontics, the bracket comprising:
    a retention bracket base (1) comprising: bracket base grooves (6) having a top, a bottom, a depth, and a width; and supporting strips (5) having a width, wherein the width of said bracket base grooves (6) is smaller than the width of said supporting strips (5);
    a body (2), wherein said body comprises an arch wire slot (3) having a top, a base, and sides and wings for ligatures (4, 4') having a top, a bottom, and sides, wherein the bracket is made from polycarbonate, polysulfone, or polyethersulfone;
    an injection spot located in the center of the retention bracket base;
    wherein the bracket is entirely made of plastic by an injection molding process;
    wherein the body has:
    an occlusal-gingival length ($I_1$) which ranges from 3.3 mm to 4.5 mm;
    a mesial-distal length ($I_2$) which ranges from 2.8 mm to 3.6 mm;
    a distance ($I_3$) from the bottom of the bracket base groove (6) to the base of the arch wire slot which ranges from 0.9 mm to 2.0 mm; and
    a distance ($I_4$) from the an intersection of lateral and bottom sides of the body to a surface of the arch wire slot of the ligature which ranges from 0.7 mm to 2.0 mm;
    wherein the bracket base grooves (6) comprises two lateral walls (17) and a posterior-wall (9), wherein said lateral walls (17) are defined by an external curvature radius ($r_1$), an internal curvature radius ($r_2$) and a gap distance between centers (d),
    wherein the posterior wall (9) has a concave form with an inner curvature radius;
    wherein said supporting strips (5) comprises the lateral walls (17) and an anterior wall (10), wherein said anterior wall (10) has a concave form with an external curvature radius; and
    wherein the radius of curvature of the anterior wall is greater than the radius of curvature of the posterior wall.

2. The bracket according to claim 1, wherein the retention bracket base (1) comprises between 3 to 6 bracket base grooves (6);
    wherein the width of said bracket base groove ranges from 0.2 mm to 0.4 mm;
    wherein the width of the supporting strips ranges from 0.45 mm to 1 mm;
    wherein the depth in the center of the bracket ranges from 0.5 mm to 0.7 mm; and
    the depth of said bracket base groove (6) depends on the values of the external curvature radius ($r_1$) and the internal curvature radius ($r_2$) as well as on the distance between centers (d), wherein $6 < r_1 \leq 20$, $2 \leq r_2 \leq 5$ and $r_2 \leq (r_1 - 2)$.

3. A method for making a bracket for its use in orthodontics, the bracket for orthodontics comprising:
    a retention bracket base (1) comprising bracket base grooves (6) having a top, a bottom, and a width; supporting strips (5) having a width, wherein the width of said bracket base grooves (6) is smaller than the width of said supporting strips (5); a body, wherein said body comprises an arch wire slot (3) having a top, a base, and sides and wings for ligatures (4, 4') having a top, a bottom, and sides;
    an injection spot located in the center of the retention bracket base;
    wherein the bracket is made from polycarbonate, polysulfone, or polyethersulfone;
    wherein the body has:
    an occlusal-gingival length ($I_1$) which ranges from 3.3 mm to 4.5 mm;
    a mesial-distal length ($I_2$) which ranges from 2.8 mm to 3.6 mm;
    a distance ($I_3$) from the bottom of the bracket base groove (6) to the base of the arch wire slot which ranges from 0.9 mm to 2.0 mm; and
    a distance ($I_4$) from the an intersection of lateral and bottom sides of the body to a surface of the arch wire slot of the ligature which ranges from 0.7 mm to 2.0 mm;
    wherein the retention bracket base (1) has a concave form;
    wherein the bracket base grooves (6) comprises two lateral walls (17) and a posterior wall (9) having a concave form; and
    wherein the supporting strips (5) are comprised of the lateral walls (17) and an anterior wall (10) having concave form;
    the method comprising:
    a) fabricating a mold having a mold male (11) to conform the retention bracket base (1); a mold cavity (12) to conform the body (2); and a slide system; wherein said mold male (11) includes a sole plastic injection spot (7) located on the geometric center of the bracket base (1), and exhaust spots for gases (14) of the base (1), wherein the mold cavity includes exhaust spots for gases (15); wherein said mold male (11) has a reinforcing rib surrounding said plastic injection spot (7), wherein the reinforcing rib is positioned perpendicularly between the lateral bracket walls (17) to be conformed;
    b) filling the mold cavity (12) with melted flowed plastic material through said injection spot (7);
    c) compacting and cooling the filled mold cavity;
    d) ejecting the retention bracket base aided by said slide system separating said mold male (11) from said mold cavity (12), and e) treating the retention bracket base (1) by a corundum blasting with particles of a size ranging from 120 to 180 microns under a 20 psi pressure, at a distance of 10 cm, during 2 seconds.

4. A bracket for its use in orthodontics comprising:

a retention bracket base (1) comprising bracket base grooves (6) having a top, a bottom, and a width; supporting strips (5) having a width, wherein the width of said bracket base grooves (6) is smaller than the width of said supporting strips (5); a body, wherein said body comprises an arch wire slot (3) having a top, a base, and sides and wings for ligatures (4, 4') having a top, a bottom, and sides;

an injection spot located in the center of the retention bracket base;

wherein the bracket is made from plastic injection molding;

wherein the retention bracket base (1) has a concave form;

wherein the bracket base grooves (6) comprises two lateral walls (17) and a posterior wall (9) having a concave form with a curvature;

wherein the supporting strips (5) is comprised of the lateral walls (17) and an anterior wall (10) having concave form with a curvature; and wherein the radius of curvature of the anterior wall is greater than the radius of curvature of the posterior wall.

* * * * *